United States Patent
Yu et al.

(10) Patent No.: US 7,805,997 B2
(45) Date of Patent: Oct. 5, 2010

(54) ON-MACHINE METHOD FOR DETERMINING TRANSMISSION SHAFT ASSEMBLY QUALITY

(75) Inventors: Linxiao Yu, Peoria, IL (US); Gary P. Shandley, Normal, IL (US); Ginger Cunningham, Peoria, IL (US); Dong Fei, Peoria, IL (US); Douglas A. Rebinsky, Peoria, IL (US)

(73) Assignee: Caterpillar Inc, Peoria, IL (US)

( * ) Notice: Subject to any disclaimer, the term of this patent is extended or adjusted under 35 U.S.C. 154(b) by 372 days.

(21) Appl. No.: 12/106,623

(22) Filed: Apr. 21, 2008

(65) Prior Publication Data

US 2009/0260441 A1    Oct. 22, 2009

(51) Int. Cl.
*G01N 29/06* (2006.01)
*G01N 29/48* (2006.01)

(52) U.S. Cl. .............................. 73/622; 73/620; 73/627

(58) Field of Classification Search .................. 73/620, 73/622, 627
See application file for complete search history.

(56) References Cited

U.S. PATENT DOCUMENTS

| | | | | | |
|---|---|---|---|---|---|
| 3,228,233 | A | * | 1/1966 | Keldenich | 73/622 |
| 3,732,726 | A | * | 5/1973 | Ferber | 73/601 |
| 3,924,453 | A | * | 12/1975 | Clark et al. | 73/622 |
| 3,978,714 | A | | 9/1976 | Shraiber et al. | |
| 4,893,511 | A | * | 1/1990 | Voigt et al. | 73/622 |
| 4,899,590 | A | * | 2/1990 | Light et al. | 73/622 |
| 4,975,855 | A | * | 12/1990 | Miller et al. | 702/35 |
| 4,988,979 | A | | 1/1991 | Sasaki et al. | |
| 5,068,800 | A | * | 11/1991 | Brook et al. | 702/36 |
| 5,078,954 | A | | 1/1992 | Smith et al. | |
| 5,125,272 | A | | 6/1992 | Latimer et al. | |
| 5,511,425 | A | | 4/1996 | Kleinart et al. | |
| 5,533,400 | A | | 7/1996 | Gasch et al. | |
| 5,625,511 | A | * | 4/1997 | Brooks et al. | 360/99.08 |
| 5,942,690 | A | | 8/1999 | Shvetsky | |
| 6,065,344 | A | | 5/2000 | Nolan | |
| 6,349,252 | B1 | | 2/2002 | Imanishi et al. | |
| 6,640,632 | B1 | | 11/2003 | Hatanaka et al. | |
| 6,640,634 | B2 | | 11/2003 | Hashimoto et al. | |
| 7,093,490 | B2 | | 8/2006 | Kono et al. | |
| 7,174,788 | B2 | | 2/2007 | Czerw et al. | |
| 2007/0044555 | A1 | | 3/2007 | Busch et al. | |
| 2009/0320599 | A1 | * | 12/2009 | Burat et al. | 73/622 |
| 2010/0031751 | A1 | * | 2/2010 | Perkins et al. | 73/622 |

FOREIGN PATENT DOCUMENTS

JP    11023540 A  *  1/1999

* cited by examiner

*Primary Examiner*—Hezron Williams
*Assistant Examiner*—Rose M Miller
(74) *Attorney, Agent, or Firm*—Leydig, Voit & Mayer

(57) ABSTRACT

An on-machine inspection method for detecting whether a shaft of a transmission system has failed uses a test probe from flaw detection apparatus to discover echo signals with known peaks corresponding to defined weakened portions in the shaft. The test probe is then moved to prescribed angular distances about an end face of the shaft to obtain the echo signals.

7 Claims, 7 Drawing Sheets

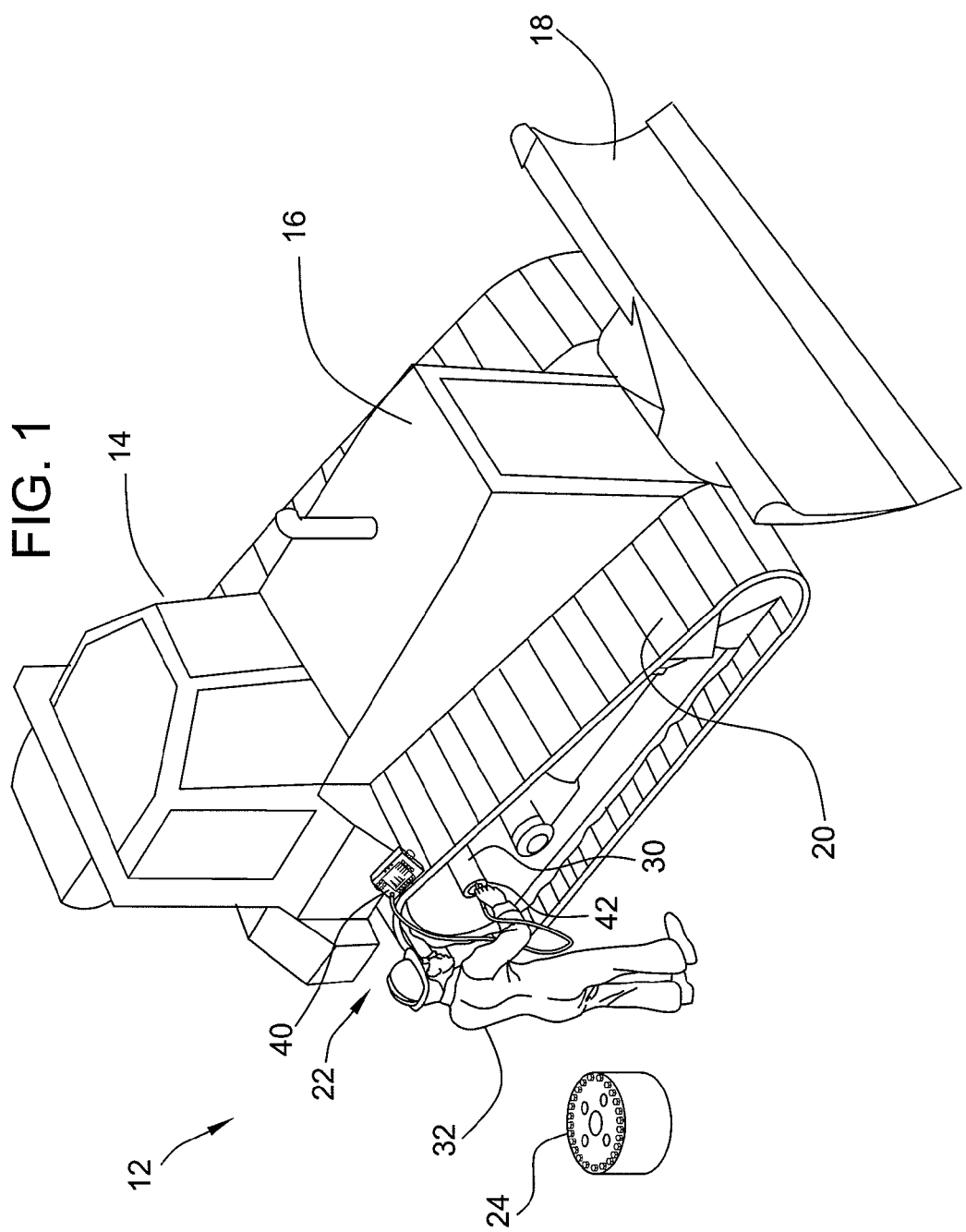

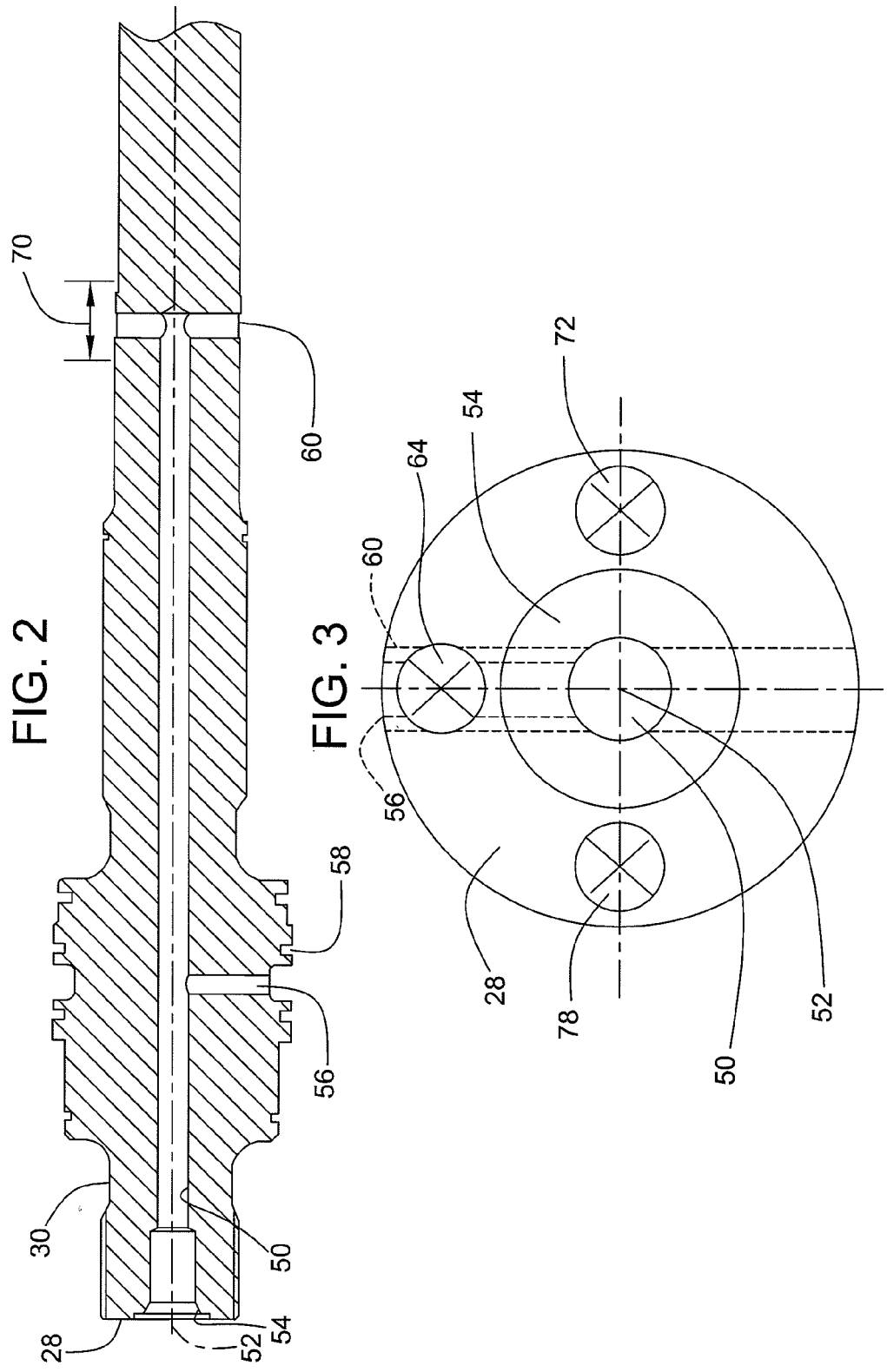

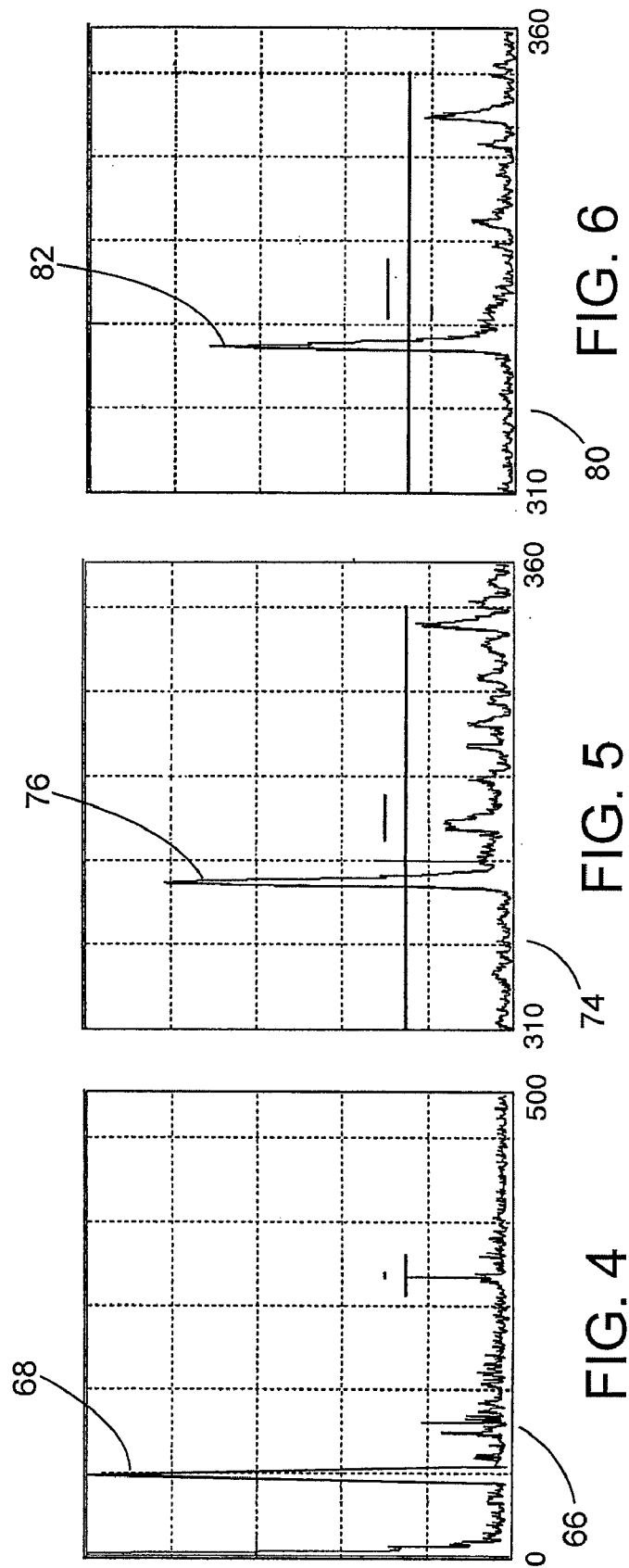

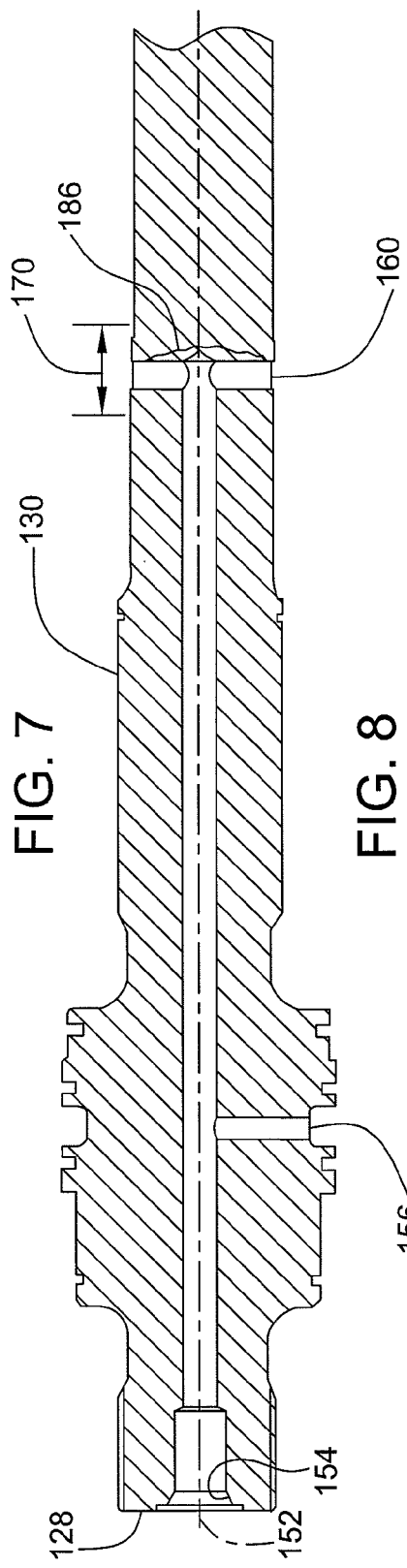
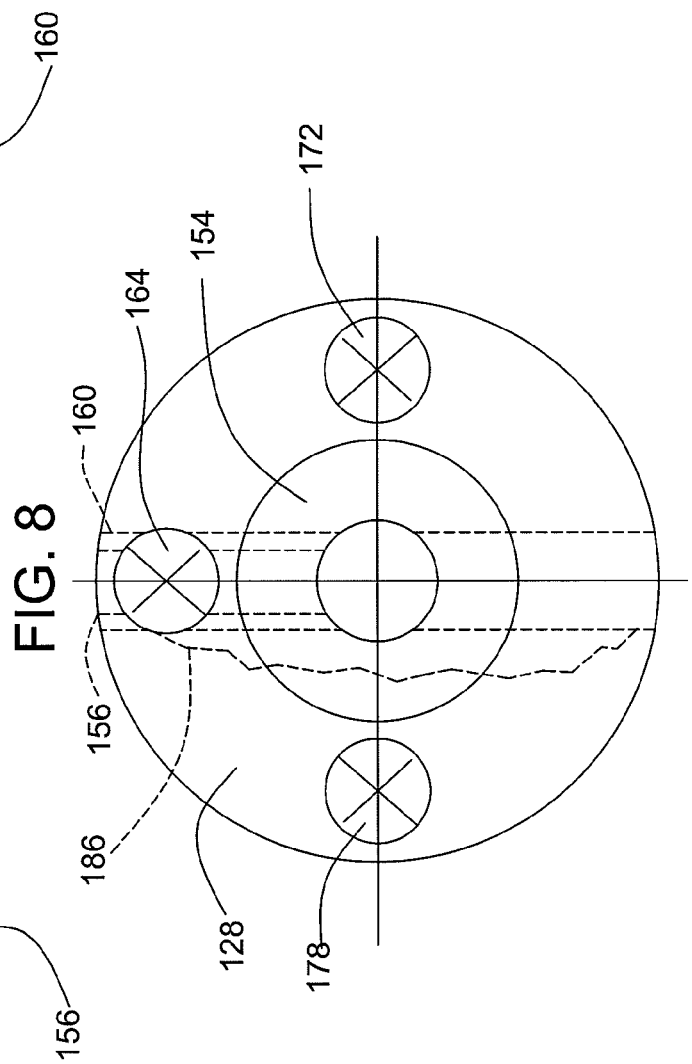

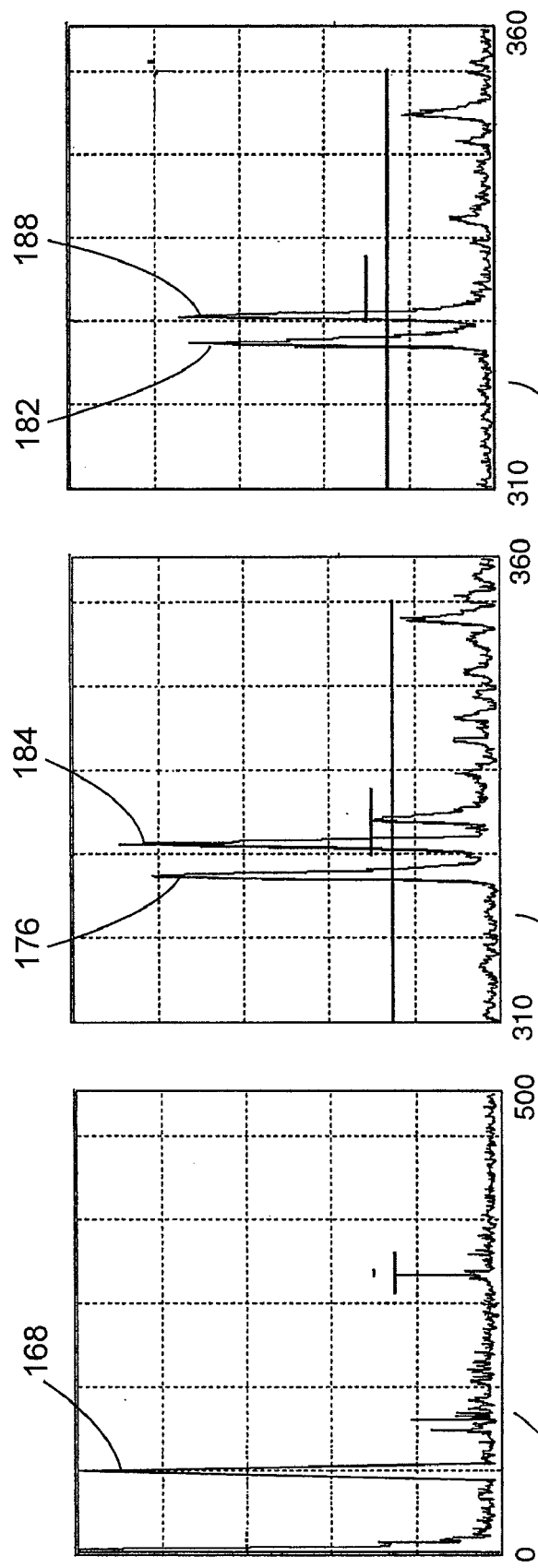

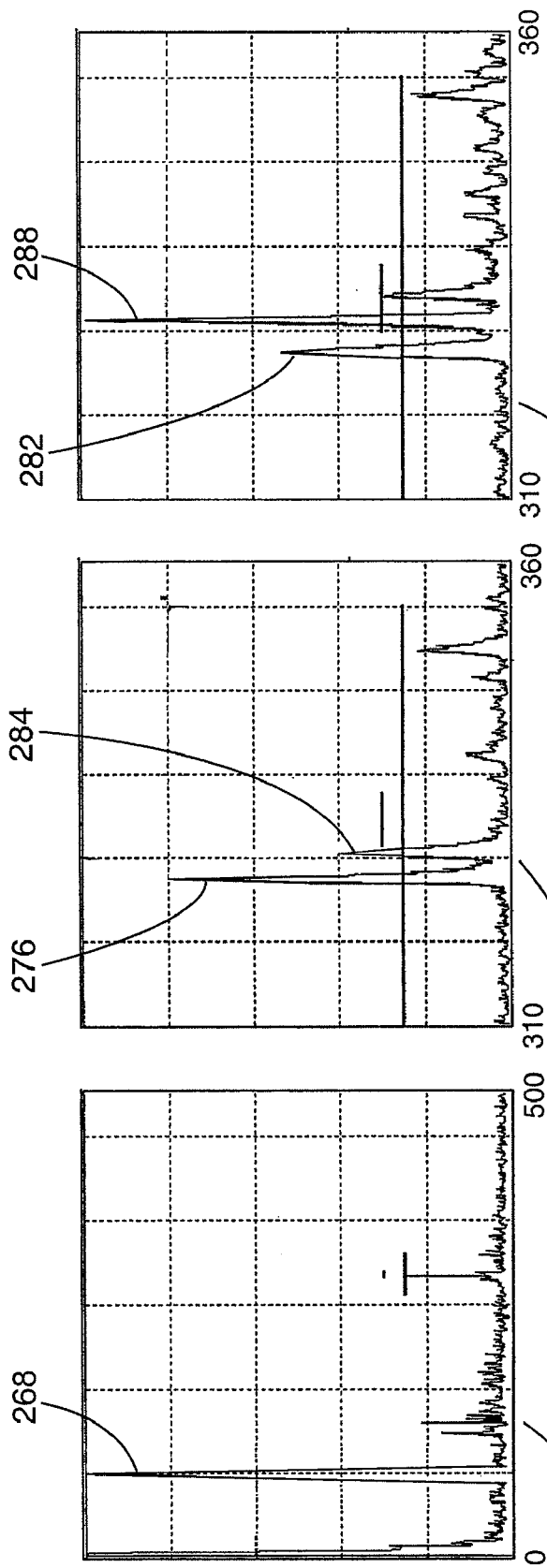

ON-MACHINE METHOD FOR DETERMINING TRANSMISSION SHAFT ASSEMBLY QUALITY

TECHNICAL FIELD

This patent disclosure relates generally to testing and analysis procedures for machines, and more particularly, to an inspection procedure that determines whether a failure has occurred in a shaft which is located in the machine.

BACKGROUND

Components in transmission systems of heavy-duty machines are often subjected to abnormal torque and other forces during operation. Specifically, a transmission shaft in such a transmission system is often susceptible to excessive wear. Also, improper manufacturing processes, such as inadequate heat treatment or the like, may also be the cause of early failure of the transmission shaft. For these reasons, a transmission shaft sometimes experiences cracks and other failures despite advanced metallurgical processing techniques and other engineering approaches that are used to avoid such failures. In general, a transmission shaft failure will cause failure of the machine as a whole. This creates excessive idle-time costs to operators of such machines. Accordingly, it is important that such machines are in service as much as possible.

Various methodologies for testing transmission systems are known in the art. For example, ultrasonic flaw detection apparatus may be used to detect cracking and other defects in materials, such as is described in U.S. Pat. No. 5,511,425, entitled "Flaw Detector Incorporating DGS." The described flaw detector involves generation of a sound wave or pulse and transmitting the pulse through a transducer to the material under inspection. The transducer then listens for an echo signal that provides information concerning the material under consideration. However, these flaw detectors are often used in test procedures that involve disassembly of the transmission system in order to inspect the various components in detail. While this is suitable for discovering cracking or other failures in the transmission shaft, such procedures are somewhat costly and often time consuming. They further require skilled personnel in order to perform the testing.

BRIEF SUMMARY OF THE DISCLOSURE

The present disclosure relates to an inspection method for detecting whether a shaft of a transmission system of a machine has failed with reduced disassembly of the transmission system. The method is particularly suited for a transmission shaft having a first defined weakened portion, disposed at a first distance from an end face of the shaft, and a second defined weakened portion, disposed at a second distance from the end face of the shaft and at a known orientation with respect to the first defined weakened portion. The method includes exposing the end face of the transmission shaft. Next, a test probe of a flaw detection apparatus is placed on the end face. The test probe is scanned about the periphery of the end face to discover a first echo signal with a first peak corresponding to the first defined weakened portion. The first signal is maximized and the flaw detection apparatus is tuned to obtain a second echo signal.

The test probe is then moved a prescribed angular distance from the first location on the end face. The angular distance in this case is sufficient to obtain a first peak from the second signal corresponding to the second defined weakened portion located within the shaft. At this location, a scan is performed in a narrow longitudinal window with respect to the second defined weakened portion. After detection information is obtained, the test probe is placed at a third location, located at the prescribed angular distance in an opposite direction from the second location. The test probe obtains flaw detection information within the same longitudinal window at this location.

The detection information developed with respect to the second defined weakened location is analyzed to determine whether any further peak signals in the echo signals were obtained. If any such signals were obtained, the method determines that the axial component has failed and further corrective action is required. The method thus provides an on-machine non-destructive analysis procedure that can be implemented in a field environment.

BRIEF DESCRIPTION OF THE DRAWINGS

FIG. 1 is a simplified view of a machine with a test operator nearby performing an on-machine inspection procedure according to the disclosure;

FIG. 2 is a simplified section view of a transmission shaft used in a transmission assembly in the machine of FIG. 1 on which an inspection procedure according to the disclosure may be performed;

FIG. 3 is an end view of the transmission shaft shown in FIG. 2 illustrating test probe locations according to the inspection procedure;

FIGS. 4, 5 and 6 are graphical representations illustrating the detection of various peak signals in the transmission shaft of FIGS. 2 and 3, denoting that the shaft successfully passed the inspection procedure;

FIG. 7 is a further transmission shaft that has experienced a failure due to cracking therein;

FIG. 8 is an end view of the transmission shaft of FIG. 7, illustrating cracking from an end view;

FIGS. 9, 10, and 11 are graphical representations illustrating the detection of various peak signals in the transmission shaft of FIGS. 7 and 8, denoting that the shaft failed the inspection procedure;

FIGS. 12, 13, and 14 are graphical representations illustrating the detection of various peak signals in a further transmission shaft that has failed the inspection procedure of this disclosure.

DETAILED DESCRIPTION

Figure 15:
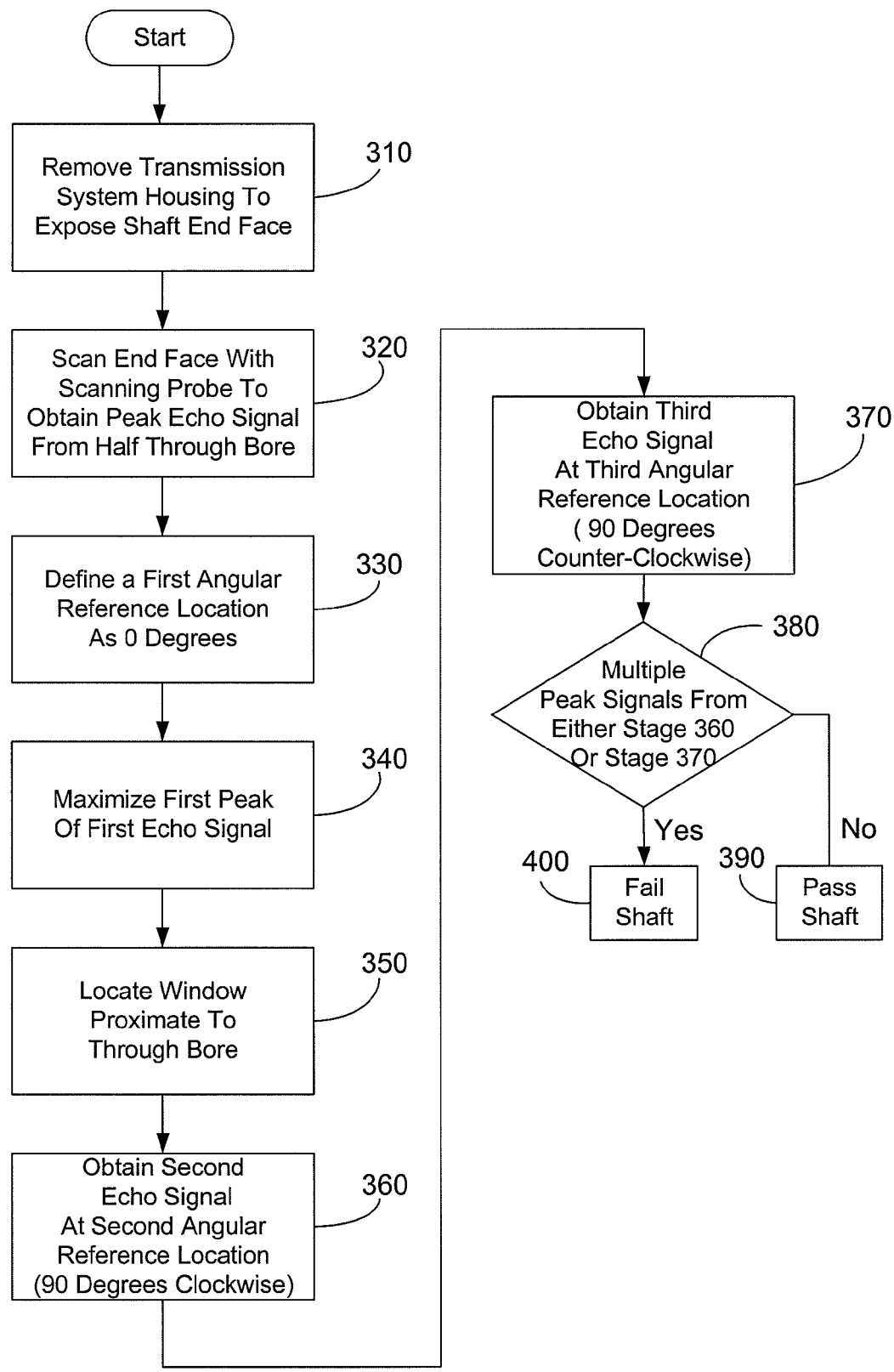
FIG. 15 is a flow diagram illustrating the steps performed according to the inspection procedure of the disclosure.

The present disclosure relates to an inspection procedure for detect cracking and other failures of specific transmission components while they are in service. The inspection procedure may be used without fully disassembling the transmission system and without requiring skilled personnel to perform analysis of the component. The disclosed inspection method may thus provide an indication of whether a transmission component has passed or failed without removing the shaft and performing laboratory experiments thereon. In this way, a machine owner or operator may obtain a greater understanding of the operating conditions of the machine in a reduced amount of time and cost.

FIG. 1 is a simplified diagram illustrating an environment in which an inspection procedure according to the disclosure may be performed. More specifically, a machine 12 such as a bulldozer may include an operator station 14, an engine compartment 16, a blade 18 and a track-type drive system 20. The machine 12 includes a transmission system, generally denoted by the numeral 22, for providing output torque to the drive system 20. The transmission system 22 is enclosed within a transmission housing 24. The transmission housing 24 contains a plurality of gear sets that operate in a known fashion. This configuration is typical for off-road equipment, but other configurations are also known.

The transmission housing 24 is removed to expose an end face 28 of a transmission shaft 30, as best seen in FIGS. 2 and 3. An operator 32 conducts the inspection procedure in this case with the use of a flaw detection apparatus 40. As explained in greater detail below, the operator 32 locates a test probe 42 flush with the end face 28 of the transmission shaft 30 according to a prescribed sequence of operations. In this way, the operator 32 may readily determine whether the transmission shaft 30 contains a crack or other flaw.

In an embodiment, the flaw detection apparatus 40 is a portable ultrasonic flaw detector, such as a type USN 60 Portable Flaw Detector manufactured by Krautkramer Ultrasonic Systems. While this particular model and type of detection apparatus is not required to incorporate the features of the disclosure, various advantages flow from utilization of a portable detection apparatus of this general type. For example, the use of ultrasonic signals permits the visualization of defects in the transmission shaft 30, while attenuating artifacts that may otherwise result in spurious indications. Their relatively small size and widespread availability further enables the procedures disclosed herein to be readily practiced, even in remote areas where the machine 12 is often placed into use. Also, ease of use of this type of detection apparatus enables non-skilled and semi-skilled operators to readily practice the disclosure.

The test probe 42 used in conjunction with the flaw detection apparatus 40 is a relatively small sensor probe in an embodiment. In an illustrated embodiment, the test probe 42 is an ultrasonic transducer that emits a 5 MHz signal, and has a probe diameter of approximately 0.25 inches. Other probe arrangements are also contemplated.

FIGS. 2 and 3 illustrate the transmission shaft 30 to be inspected. FIG. 2 is a simplified section view of the transmission shaft 30 and FIG. 3 is an end view. As noted above, the end face 28 defines one of the ends of the transmission shaft 30. The end face 28 in this case is generally disc-shaped and provides a relatively planar surface when exposed from the transmission housing 24. The transmission shaft 30 further includes a central bore 50 that extends longitudinally along a central axis 52 through a portion of the transmission shaft 30. A chamfered portion 54 is interposed between the end face 28 and the central bore 50.

As best seen in FIG. 2, the transmission shaft 30 includes a first defined weakened portion or a half-through bore 56 that is spaced a known distance from the end face 28. In an embodiment, the half-through bore 56 is located at approximately 110 mm from the end face 28. The half-through bore 56 is located at a shoulder portion 58 of the transmission shaft 30. As shown in FIGS. 2 and 3, the half-through bore 56 is laterally offset with respect to the central axis 52, although the half-through bore 56 intersects with the central bore 50 in the illustrated embodiment.

A second defined weakened portion or through-bore 60 is longitudinally spaced at a known distance from the half-through bore 56 and from the end face 28. In the illustrated embodiment, the though-bore 60 is located approximately 327 mm from the end face 28. The through-bore 60 is laterally spaced from the half-through bore and from the central axis 52. It has been found that cracking and other defects in the transmission shaft 30 due to the application of torque and other stresses often occur within a relatively small longitudinal window that is proximate to the through-bore 60. Specifically, such cracking typically may initialize from the wall defining the through-bore 60, as shown by the formation of a crack 186 formed in a transmission shaft 130 in FIGS. 7 and 8.

A method according to the disclosure provides an in-machine inspection of the transmission shaft 30 by performing a prescribed sequence of steps. First, the transmission housing 24 is removed from the machine so that the end face 28 of the transmission shaft 30 is exposed to the operator 32. Next, the operator 32 places the test probe 42 of the flaw detection apparatus 40 onto the end face 28. The test probe 42 is scanned 360-degrees about the periphery of the end face 28 to obtain a peak echo signal from the flaw detection apparatus 40. The peak echo signal corresponds approximately to the angular orientation of the half-through bore. The method denotes this location as a first angular reference location 64 shown in FIG. 3. In an illustrated embodiment, the first angular reference location 64 is recorded as 0 degrees.

FIG. 7 illustrates a graphical output of an echo signal amplitude obtained as a function of distance, as provided by the flaw detection apparatus 40. An output echo signal 66 in this case was obtained at the first angular reference location 64 by scanning the end face 28 of the transmission shaft 30 shown in FIGS. 2 and 3. As shown, the displayed output echo signal 66 has a first peak 68 at approximately 110 mm from the end face 28, at the distance of the half-through bore 56.

The peak signal obtained at the first angular reference location 64 thus approximates the location of the first weakened portion or half-through bore 56. Because the half-through bore is located relatively near to the end face 28, the first peak 68 of the output echo signal 66 can be readily perceived by the flaw detection apparatus 40. Thus, the flaw detection apparatus 40 can be adjusted so that the amplitude of the first peak 68 is approximately full scale of the display.

The method uses the obtained scan information concerning the angular location of half-through bore 56, i.e., the first angular reference location 64, and the known distance between the half-through bore 56 and the through bore 60, to locate a relatively narrow window proximate to the through bore 60. Because the through bore 60 is disposed at a known angular orientation with respect to the half-through bore 56, the first angular reference location 64 is used to peak the echo signal of the through bore 60. In the illustrated embodiment, the through bore 60 is longitudinally spaced from the half-through bore 56 at a distance of about 217 mm. For obtaining scan information proximate to the through bore 60, the operator 32 adjusts the flaw detection apparatus 40 to magnify echo signals obtained in a longitudinal window (numeral 70 in FIG. 2) extending to either side of the through bore 60. For example, the operator may magnify the echo signals within a longitudinal window of approximately 50 mm.

The operator 32 then performs a next stage by moving the test probe 42 to a second angular reference location 72 on the end face 28 of the transmission shaft 30. The second angular reference location 72 is an angular distance that is a prescribed number of degrees from the first angular reference location 64. In this case, the operator moves the test probe 42 to the second angular reference location 72 by positioning the test probe 42 at a location that is approximately 90 degrees in a clock-wise direction from the first angular reference location 64.

At the second angular reference location 72, the operator 32 adjusts the flaw detection apparatus 40 to display a second output echo signal 74 with a first peak 76 to approximately 80 percent full screen display, as shown in FIG. 8. The first peak 76 obtained from the through bore 60 is displayed within a longitudinal window of 50 mm in this embodiment.

At a next stage, the operator rotates the location of the test probe 42 to a third angular reference location 78 on the end face 28. The third angular reference location 78 is an angular distance that is a prescribed number of degrees from the first angular reference location 64, in a direction opposite the second angular reference location 72. For example, the operator 32 may move the test probe 42 to the third angular reference location 78 by positioning the probe 42 at a location that is approximately 90 degrees in a clock-wise direction from the first angular reference location 64. At the third angular reference location 78, the operator 32 obtains scan information and displays a third output echo signal 80 with a first peak 82, as shown in FIG. 7. The first peak 82 of the third output echo signal 80 also is obtained as a result of the contribution of the through bore 60 with respect to the displayed echo signal. In this case, the amplitude of the first peak 82 of the third output echo signal 80 may be different than that of the first peak 76 of the second output echo signal 74 due to the difference in orientation of the third location with respect to the through bore 60. In the absence of any other peaks in the signal that exceed a threshold which are obtained from the longitudinal window 70 (and as displayed in FIGS. 6 and 7), the transmission shaft 30 is considered to have passed the on-machine inspection procedure.

FIGS. 5 and 6 illustrate a transmission shaft 130, having numerals corresponding to like elements for the transmission shaft 30 shown in FIGS. 2 and 3 except that they include the prefix "1". In this case, the procedure for inspecting the transmission shaft 130 would similarly begin by scanning an end face 128 of the transmission shaft 130 with a flaw detection apparatus 40 to obtain a first angular reference location 164 in the same manner as described above. As shown in FIG. 9, an output echo signal 166 is provided with a first peak 168 corresponding to a half-through hole 156 in the transmission shaft 130. After the first peak 168 is determined and maximized, the operator next rotates the test probe to a second angular reference position 172 on the end face 128, disposed at an angular orientation of 90 degrees with respect to the first angular reference location 164.

In this example, a second output echo signal 174 obtained with respect to a longitudinal window 170 (see FIG. 7) provides a first peak 176 as well as a second peak 184. The second peak 184 of the second output echo signal 174 indicates that a crack 186 (see FIGS. 5 and 6) or other flaw proximate to the through hole 160 has been detected. The presence of the crack 186 is confirmed at a next stage in which the test probe 42 is moved to a third angular reference location 178, disposed at an angular orientation of approximately 90 degrees counter-clockwise with respect to the first angular reference location 164. As shown in FIG. 10, a third output echo signal 180 obtained by the flaw detection apparatus 40 exhibits a first peak 182 and a second peak 188. The second peak 188 provides confirmation that the transmission shaft 130 has failed.

FIGS. 12, 13 and 14 illustrate output echo signals obtained by inspecting a third transmission shaft (not shown) according to the disclosed inspection method. Similarly, the output echo signals have numerals corresponding to like elements with respect to the echo signals shown in FIGS. 5, 6 and 7 and 9, 10 and 11, except that they include the prefix "2." At a first angular reference location (not shown), an output echo signal 266 is provided with a first peak 268 corresponding to a half-through hole in the transmission shaft as is shown in FIG. 12. Next, a second output echo signal 274 is obtained at a second angular reference location, oriented 90 degrees in a clockwise direction with respect the first angular reference location. The second output echo signal 274 provides a first peak 276 as well as a second peak 284, as shown in FIG. 13.

The presence of a crack is further confirmed at a next stage in which the test probe 42, located at the third angular reference location, oriented approximately 90 degrees counter-clockwise with respect to the first angular reference location, provides an echo signal 280 as shown in FIG. 14. Specifically, the echo signal 280 obtained by the flaw detection apparatus 40 exhibits a first peak 282 and a second peak 288. The second peak 288 of the third output echo signal obtained at this orientation provides a confirmation that the transmission shaft 130 has failed. In this way, the presence of a "double peak" signature from either side will fail the transmission shaft 130.

FIG. 15 is a flow diagram illustrating a sequence of steps according to the disclosure. At a preliminary stage 310, an operator removes a transmission housing from the machine to expose an end face of a transmission shaft. At a first inspection stage 320, the operator scans the end face with a test probe of flaw detection apparatus. The end face may be scanned 360-degrees about a periphery of the end face 28 to obtain a peak echo signal. As noted above, the peak echo signal corresponds approximately to the angular orientation of the half-through bore formed in the transmission shaft. At a further stage 330, the operator denotes the angular location of the first peak signal as a first angular reference location. This first angular reference location may be recorded as 0 degrees. At a next adjustment stage 340, the first peak of the echo signal is maximized. The first peak may then be adjusted to approximately full scale of the display.

The method uses the obtained scan concerning the first angular reference location to locate a relatively narrow window proximate to the through bore at a location stage 350. The method then proceeds to a second inspection stage 360 by moving the test probe to a known angular offset from the first angular reference location, such as 90 degrees in an embodiment. At the second inspection stage 360, the flaw detection apparatus obtains scan information in a longitudinal window proximate to a through-bore of the transmission shaft, located at a known distance from the half-through bore. At the second angular reference location, the operator adjusts the flaw detection apparatus to display a second echo signal with a second peak corresponding to the through bore to approximately 80 percent full screen display.

At a third inspection stage 370, the operator rotates the location of the test probe to a third angular reference location, e.g., 90 degrees counter-clockwise from the first angular reference location. At this angular reference location, the operator obtains scan information and displays a third echo signal with a third peak, also corresponding to the through bore. The third peak also is obtained as a result of the contribution of the through bore with respect to the displayed echo signal. The method then determines whether any further peak signals are obtained at either of stages 360 or 370 at a decision stage 380. If not, the transmission shaft is considered to have passed the inspection procedure. Otherwise, when further peak signals are detected at either of stages 360 or 370, the transmission shaft is considered to have failed the inspection procedure. The operator is thus required to take further corrective action.

INDUSTRIAL APPLICABILITY

The industrial applicability of the inspection process used to inspect a transmission shaft while it remains intact in a transmission system for a machine will be readily appreciated from the foregoing discussion. As described, an inspection method based on an application of ultrasonic signals to an end face of the transmission shaft and detecting the resultant echo signals provides output information that can be used to discriminate among operative and inoperative transmission shafts. The obtained information may be used to determine whether the transmission system requires a shaft replacement or other corrective action is required. Advantageously, the disclosure may be used by semi-skilled and even non-skilled personnel to readily determine the condition of the transmission shaft.

The present disclosure is applicable to detect whether cracks exist in various types of transmission shafts. That is, with appropriate modification of the method, the condition of transmission shafts of different configurations and known reference locations may be determined. The present disclosure provides a relatively low cost data gathering apparatus and method that avoids laboratory or similar metallurgical analysis of the transmission shaft. In addition, it is relatively simple to operate. The disclosure may thus be employed in field conditions in which engineering staff are not readily available. One possible and representative procedure is outlined below for the purpose of illustration by way of example.

It will be appreciated that the foregoing description provides examples of the disclosed inspection method. It is contemplated that other implementations of the disclosed principles will differ in detail from the foregoing examples. All discussions of specific examples are intended to reference the particular example being discussed at that point and are not intended to imply any limitation as to the scope of the present disclosure more generally. All language of distinction and disparagement with respect to certain features is intended to indicate a lack of preference for those features, but not to exclude such from the scope of the disclosed principles entirely unless otherwise indicated.

Accordingly, the disclosed innovations includes all modifications and equivalents of the subject matter recited in the claims appended hereto as permitted by applicable law. Moreover, any combination of the above-described steps and elements in all possible variations thereof is encompassed unless otherwise indicated herein or otherwise clearly contradicted by context.

We claim:

1. A method for detecting the presence of a crack in a shaft, the shaft including at least a first preformed weakened portion, disposed at a first distance from an end face of the shaft, and a second preformed weakened portion, disposed at a second distance from the end face of the shaft, the method comprising the steps of:
   exposing the end face of the shaft while the shaft is located within the machine,
   scanning the end face of the shaft with a test probe of a flaw detection apparatus to obtain a first echo signal having a first peak amplitude corresponding to the first preformed weakened portion and denoting a first angular reference location,
   moving the test probe to a second angular reference location, disposed at a known angular distance from the first angular reference location,
   obtaining a second echo signal having a first peak amplitude corresponding to the second preformed weakened portion at the second angular reference location,
   moving the test probe to a third angular reference location, disposed opposite the second angular reference location at a known angular distance from the first angular reference location,
   obtaining a third echo signal having a first peak amplitude corresponding to the second preformed weakened portion at the third angular reference location, and
   determining whether a second peak amplitude is present in the second echo signal obtained at the second angular location or whether a second peak amplitude is present in the third echo signal obtained at the third angular reference location.

2. The method of claim 1 further comprising the step of:
   failing the shaft when either whether the second peak amplitude is present in the second echo signal or whether the second peak amplitude is present in the third echo signal.

3. The method of claim 1 further comprising the step of:
   passing the shaft when a second peak amplitude is not present in the second echo signal and when a second peak amplitude is not present in the third echo signal.

4. The method of claim 1 wherein the first angular reference location is denoted as 0 degrees.

5. The method of claim 4 wherein the second angular reference location is denoted as approximately 90 degrees clockwise from the first angular reference location.

6. The method of claim 5 wherein the third angular reference location is denoted as approximately 90 degrees counter-clockwise from the first angular reference location.

7. A method for detecting with the use of a test probe operatively associated with ultrasonic flaw detection apparatus the presence of a crack in a transmission shaft disposed within a machine, the shaft including a first bore disposed at a first distance from an end face of the shaft, and a second bore disposed at a second distance from the end face of the shaft which is greater than the first distance, the method comprising the steps of:
   exposing the end face of the shaft while the shaft is located within the machine,
   scanning the periphery of the end face of the shaft with the test probe to obtain an echo signal having a first peak amplitude corresponding to the first bore and denoting a first angular reference location,
   moving the test probe to a second angular reference location, disposed at about 90 degrees from the first angular reference location,
   obtaining a second echo signal having a first peak amplitude corresponding to the second bore at the second angular reference location,
   moving the test probe to a third angular reference location, disposed at about 90 degrees from the first angular reference location opposite the second angular reference location,
   obtaining a third echo signal having a first peak amplitude corresponding to the second preformed weakened portion at the third angular reference location, and
   determining whether at least a second peak amplitude is present in the second echo signal obtained at the second angular reference location or whether at least a second peak amplitude is present in the third echo signal obtained at the third angular reference location.

* * * * *